(12) United States Patent
Gillespie

(10) Patent No.: US 7,041,866 B1
(45) Date of Patent: May 9, 2006

(54) SOLID-ACID ISOMERIZATION CATALYST AND PROCESS

(75) Inventor: Ralph D. Gillespie, Gurnee, IL (US)

(73) Assignee: UOP LLC, Des Plaines, IL (US)

( * ) Notice: Subject to any disclaimer, the term of this patent is extended or adjusted under 35 U.S.C. 154(b) by 592 days.

(21) Appl. No.: 10/267,425

(22) Filed: Oct. 8, 2002

(51) Int. Cl.
  *C10G 11/02* (2006.01)
  *C07C 5/22* (2006.01)
  *B01J 27/043* (2006.01)

(52) U.S. Cl. ............ 585/750; 208/120.01; 208/120.35; 208/111.1; 208/111.01; 208/111.35; 208/137; 208/138; 208/143; 208/217; 208/251 H; 208/254 H; 585/467; 585/721; 585/670; 585/660; 585/661; 585/662; 585/663; 585/530; 585/531; 585/708; 585/470; 585/476; 585/480; 585/489; 585/640; 502/222; 502/223; 502/325; 502/326; 502/327; 502/332; 502/334; 502/349

(58) Field of Classification Search ..................... None
See application file for complete search history.

(56) References Cited

U.S. PATENT DOCUMENTS

| | | | |
|---|---|---|---|
| 2,939,896 A | 6/1960 | Myers .................... | 260/683.68 |
| 3,915,845 A | 10/1975 | Antos ......................... | 208/139 |
| 4,918,041 A | 4/1990 | Hollstein et al. ........... | 502/217 |
| 4,956,519 A | 9/1990 | Hollstein et al. ........... | 585/751 |
| 5,036,035 A | 7/1991 | Baba et al. .................. | 502/221 |
| 5,212,136 A | 5/1993 | Angstadt et al. ............ | 502/206 |
| 5,214,017 A | 5/1993 | Angstadt et al. ............ | 502/204 |
| 5,310,868 A | 5/1994 | Angstadt et al. ............ | 585/721 |
| 5,493,067 A | 2/1996 | Angstadt et al. ............ | 585/731 |
| 5,629,257 A * | 5/1997 | Umansky et al. ........... | 502/217 |
| 6,448,198 B1 * | 9/2002 | Szabo et al. ................. | 502/217 |

FOREIGN PATENT DOCUMENTS

EP  0 666 109 A1  1/1995

OTHER PUBLICATIONS

Moreno et al., "Isomerization of n-Butane over Sulfated Al- and Ga-Promoted Zirconium Oxide Catalysts. Influence of Promoter and Preparation Method" Jun. 2001, Journal of Catalysis, 203, pp. 453-465.*

Hua et al., "Promoting Effect of Al on SO4-2/MxOy (M=Zr, Ti, Fe) Catalysts", Aug. 2000, Journal of Catalysis, 196, pp. 104-114.*

Wang et al., "Isomerization of n-butane by gallium-promoted sulfated zirconia supported on MCM-41", May 2002, Green Chemistry, 4, pp. 257-260.*

Chen et al., "Ga-promoted tungstated zirconia catalyst for n-butane isomerization", Oct. 2002, Catalysis Letters, vol. 85, Nos. 3-4, pp. 177-182.*

* cited by examiner

*Primary Examiner*—Walter D. Griffin
(74) *Attorney, Agent, or Firm*—John G. Tolomei; Frank S. Molinaro; Maryann Maas

(57) ABSTRACT

A catalyst and process is disclosed to selectively upgrade a paraffinic feedstock to obtain an isoparaffin-rich product for blending into gasoline. The catalyst comprises a support of a sulfated oxide or hydroxide of a Group IVB (IUPAC 4) metal, a first component comprising at least one Group III A (IUPAC 13) component, and at least one platinum-group metal component which is preferably platinum.

25 Claims, 4 Drawing Sheets

US 7,041,866 B1

SOLID-ACID ISOMERIZATION CATALYST AND PROCESS

FIELD OF THE INVENTION

This invention relates to an improved catalytic composite and process for the conversion of hydrocarbons, and more specifically for the selective upgrading of a paraffinic feedstock by isomerization.

BACKGROUND OF THE INVENTION

The widespread removal of lead antiknock additive from gasoline and the rising fuel-quality demands of high-performance internal-combustion engines have compelled petroleum refiners to install new and modified processes for increased "octane," or knock resistance, in the gasoline pool. Refiners have relied on a variety of options to upgrade the gasoline pool, including higher-severity catalytic reforming, higher FCC (fluid catalytic cracking) gasoline octane, isomerization of light naphtha and the use of oxygenated compounds. Such key options as increased reforming severity and higher FCC gasoline octane result in a higher aromatics content of the gasoline pool at the expense of low-octane heavy paraffins.

Refiners are also faced with supplying reformulated gasoline to meet tightened automotive emission standards. Reformulated gasoline differs from the traditional product in having a lower vapor pressure, lower final boiling point, increased content of oxygenates, and lower content of olefins, benzene and aromatics. Benzene content generally is being restricted to 1% or lower, and is limited to 0.8% in U.S. reformulated gasoline. Gasoline aromatics content is likely to be lowered, particularly as distillation end points (usually characterized as the 90% distillation temperature) are lowered, since the high-boiling portion of the gasoline which thereby would be eliminated usually is an aromatics concentrate. Since aromatics have been the principal source of increased gasoline octanes during the recent lead-reduction program, severe restriction of the benzene/aromatics content and high-boiling portion will present refiners with processing problems. These problems have been addressed through such technology as isomerization of light naphtha to increase its octane number, isomerization of butanes as alkylation feedstock, and generation of additional light olefins as feedstock for alkylation and production of oxygenates using FCC and dehydrogenation. This issue often has been addressed by raising the cut point between light and heavy naphtha, increasing the relative quantity of naphtha to an isomerization unit. The performance of light-naphtha isomerization catalysts thus is increasingly important in refinery economics.

U.S. Pat. No. 2,939,896 teaches isomerization of paraffinic hydrocarbons using a catalyst containing platinum, halogen and a sulfate of aluminum, magnesium and/or zirconium deposited on activated alumina. The patent does not disclose additional metal components of the catalyst, however. U.S. Pat. No. 5,036,035 teaches a catalyst, and its use in isomerization, containing sulfated zirconium oxide or hydroxide and a platinum-group metal. The patent teaches that reduction of the platinum-group metal is not favorable.

U.S. Pat. No. 4,918,041, U.S. Pat. No. 4,956,519 and European Patent Application 0 666 109 A1 disclose a sulfated catalyst, and its use in isomerization, comprising an oxide or hydroxide of Group III or Group IV; oxide or hydroxide of Groups V, VI or VII; and oxide or hydroxide of Group VIII; '109 also discloses a component from a list of Group VIII metals and metal combinations.

U.S. Pat. No. 3,915,845 discloses a catalyst and its use comprising a platinum-group metal, Group IVA metal, halogen and lanthanide in an atomic ratio to platinum-group metal of 0.1 to 1.25. U.S. Pat. No. 5,493,067 teaches that isoparaffins and olefins are alkylated by contact with a solid superacid such as sulfated zirconia optionally containing added metals and containing added heteropolyacids or polyoxoanions.

U.S. Pat. No. 5,310,868 and U.S. Pat. No. 5,214,017 teach catalyst compositions containing sulfated and calcined mixtures of (1) a support containing an oxide or hydroxide of a Group IV-A element, (2) an oxide or hydroxide of a Group VI, VII, or VIII metal, (3) an oxide or hydroxide of a Group I-B, II-B, III-A, III-B, IV-A, V-A metal, and (4) a metal of the lanthanide series.

U.S. Pat. No. 5,212,136 discloses a solid super acid catalyst useful in alkylation processes comprising sulfated and calcined mixtures of a support of an oxide or hydroxide of a Group IV-A element, an oxide or hydroxide of molybdenum, and an oxide or hydroxide of a Group I-B, II-B, III-A, III-B, IV-B, V-A or VI-A metal other than molybdenum or a metal of the lanthanide series.

SUMMARY OF THE INVENTION

A purpose of the present invention is to provide an improved catalyst and process for hydrocarbon conversion reactions. Another purpose of the present invention is to provide improved technology to upgrade naphtha to gasoline. A more specific purpose is to provide an improved catalyst and process for the isomerization of light naphtha to obtain a high-octane gasoline component. This invention is based on the discovery that a catalyst containing ytterbium and platinum components provides superior performance and stability in the isomerization of light naphtha to increase its isoparaffin content.

A broad embodiment of the present invention is directed to a catalyst comprising a sulfated support of an oxide or hydroxide of a Group IVB (IUPAC 4) metal, preferably zirconium oxide or hydroxide, at least a first component which is a Group III A (IUPAC 13) component, and at least a second component being a platinum-group metal component. The first component preferably consists of a single Group III A (IUPAC 13) component and the second component preferably consists of a single platinum-group metal. Preferably, the first component is gallium or indium and the second component is platinum. The catalyst optionally contains an inorganic-oxide binder, especially alumina.

An additional embodiment of the invention is a method of preparing the catalyst of the invention by sulfating the Group IVB metal oxide or hydroxide, incorporating a first component, one or more Group III A (IUPAC 13) components, and the second component, a platinum-group metal, and preferably binding the catalyst with a refractory inorganic oxide.

In another embodiment, the invention comprises converting hydrocarbons using the catalyst of the invention. In yet another embodiment, the invention comprises the isomerization of isomerizable hydrocarbons using the catalyst of the invention. The hydrocarbons preferably comprise light naphtha which is isomerized to increase its isoparaffin content and octane number as a gasoline blending stock.

These as well as other embodiments will become apparent from the detailed description of the invention.

DETAILED DESCRIPTION OF THE INVENTION

Figure 1:
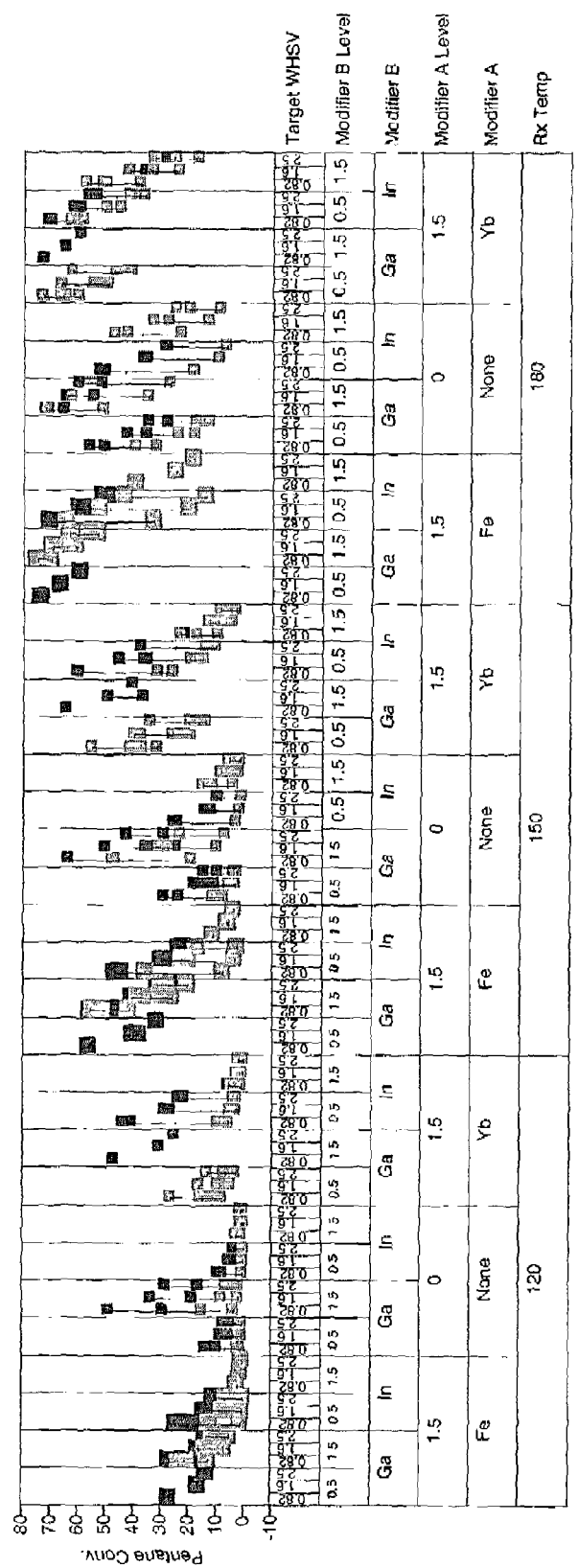
FIG. 1 is a plot of percent pentane conversion observed at different reaction temperatures and weight hourly space velocities for each of the catalysts of Example 2 having 0.25 wt-% platinum.

The support material of the catalyst of the present invention comprises an oxide or hydroxide of a Group IVB (IUPAC 4) metal, see Cotton and Wilkinson, Advanced Inorganic Chemistry, John Wiley & Sons (Fifth Edition, 1988). Preferably, the metal is selected from zirconium and titanium, with zirconium being especially preferred. The preferred zirconium oxide or hydroxide is converted via calcination to crystalline form. Sulfate is composited on the support material to form, it is believed without so limiting the invention, a mixture of Brönsted and Lewis acid sites. A component of a lanthanide-series element is incorporated into the composite by any suitable means. A platinum-group metal component is added to the catalytic composite by any means known in the art to effect the catalyst of the invention, e.g., by impregnation. Optionally, the catalyst is bound with a refractory inorganic oxide. The support, sulfate, metal components and optional binder may be composited in any order effective to prepare a catalyst useful for the conversion of hydrocarbons and particularly the isomerization of hydrocarbons.

Production of the support of the present catalyst may be based on a hydroxide of a Group IVB (IUPAC 4) metal as raw material. For example, suitable zirconium hydroxide is available from MEI of Flemington, N.J. Alternatively, the hydroxide may be prepared by hydrolyzing metal oxy-anion compounds, for example $ZrOCl_2$, $ZrO(NO_3)_2$, $ZrO(OH)NO_3$, $ZrOSO_4$, $TiOCl_2$ and the like. Note that commercial $ZrO(OH)_2$ contains a significant amount of HF, about 1 weight percent. Zirconium alkoxides such as zirconyl acetate and zirconium propoxide may be used as well. The hydrolysis can be effected using a hydrolyzing agent such as ammonium hydroxide, sodium hydroxide, potassium hydroxide, sodium sulfate, $(NH_4)_2HPO_4$ and other such compounds known in the art. The metal oxy-anion component may in turn be prepared from available materials, for example, by treating $ZrOCO_3$ with nitric acid. The hydroxide as purchased or generated by hydrolysis preferably is dried at a temperature from about 100 to 300° C. to vaporize volatile compounds.

A sulfated support is prepared by treatment with a suitable sulfating agent to form a solid strong acid. Liquid acids whose strength is greater than sulfuric acid have been termed "superacids". A number of liquid superacids are known in the literature including substituted protic acids, e.g., trifluoromethyl substituted $H_2SO_4$, triflic acid and protic acids activated by Lewis acids (HF plus $BF_3$). While determination of the acid strength of liquid superacids is relatively straightforward, the exact acid strength of a solid strong acid is difficult to directly measure with any precision because of the less defined nature of the surface state of solids relative to the fully solvated molecules found in liquids. Accordingly, there is no generally applicable correlation between liquid superacids and solid strong acids such that if a liquid super acid is found to catalyze a reaction, there is no corresponding solid strong acid which one can automatically choose to carry out the same reaction. Therefore, as will be used in this specification, "solid strong acids" are those that have an acid strength greater than sulfonic acid resins such as Amberlyst®-15. Additionally, since there is disagreement in the literature whether some of these solid acids are "superacids" only the term solid strong acid as defined above will be used herein. Another way to define a solid strong acid is a solid comprising of interacting protic and Lewis acid sites. Thus, solid strong acids can be a combination of a Bronsted (protonic) acid and a Lewis acid component. In other cases, the Bronsted and Lewis acid components are not readily identified or present as distinct species, yet they meet the above criteria.

Sulfate ion is incorporated into a catalytic composite, for example, by treatment with sulfuric acid in a concentration usually of about 0.01–10N and preferably from about 0.1–5N. Compounds such as hydrogen sulfide, mercaptans or sulfur dioxide, which are capable of forming sulfate ions upon calcining, may be employed as alternative sources. Preferably, ammonium sulfate is employed to provide sulfate ions and form a solid strong acid catalyst. The sulfur content of the finished catalyst generally is in the range of about 0.5 to 5 mass-%, and preferably is from about 1 to 2.5 mass-%, on an elemental basis. The sulfated composite is dried, preferably followed by calcination at a temperature of about 500 to 700° C. particularly if the sulfation is to be followed by incorporation of the platinum-group metal.

A first component, comprising one or more of the Group III A (IUPAC 13) components, is another essential component of the present catalyst. Included in the Group III A components are gallium, indium, thallium and mixtures thereof. Preferred components include gallium and indium. It is especially preferred that the first component consists essentially of a gallium or an indium component. The first component may in general be present in the catalytic composite in any catalytically available form such as the elemental metal, a compound such as the oxide, hydroxide, halide, oxyhalide, carbonate or nitrate or in chemical combination with one or more of the other ingredients of the catalyst. The first component is preferably an oxide, an intermetallic with platinum, a sulfate, or in the zirconia lattice. The materials are generally calcined between 600 and 700° C. and thus in the oxide form. Although it is not intended to so restrict the present invention, it is believed that best results are obtained when the first component is present in the composite in a form wherein substantially all of the first component is in an oxidation state above that of the elemental state such as in the form of the oxide, oxyhalide or halide or in a mixture thereof and the subsequently described oxidation and reduction steps that are preferably used in the preparation of the instant catalytic composite are specifically designed to achieve this end. The Group III A component can be incorporated into the catalyst in any amount which is catalytically effective, suitably from about 0.01 to about 10 mass-% lanthanide or yttrium, or mixtures, in the catalyst on an elemental basis. Best results usually are achieved with about 0.5 to about 5 mass-% of the Group III A component, calculated on an elemental basis. The preferred atomic ratio of Group III A component to platinum-group metal for this catalyst is at least about 1:1, preferably about 2:1 or greater, and especially about 5:1 or greater.

The first component is incorporated in the catalytic composite in any suitable manner known to the art, such as by coprecipitation, coextrusion with the porous carrier material, or impregnation of the porous carrier material either before, after, or simultaneously with sulfate though not necessarily with equivalent results. For ease of operation, it is preferred to simultaneously incorporate the first component with the sulfate. It is most preferred to incorporate the platinum-group metal component last. As to the Group III A component and the platinum-group metal, the order between the two does not have a significant impact.

One method of depositing the first component involves impregnating the support with a solution (preferably aqueous) of a decomposable compound of the Group III A component. By decomposable is meant that upon heating, the Group III A component is converted to the Group III A element or oxide with the release of byproducts. Illustrative of the decomposable compounds without limitation of the first component are suitable Group III A complexes or compounds such as, nitrates, halides, sulfates, acetates, organic alkyls, hydroxides, and the like compounds. Conditions for decomposition include temperatures ranging up to about 7000° C. The first component can be impregnated onto the carrier either prior to, simultaneously with, or after the platinum-group metal component, although not necessarily with equivalent results. If a sequential technique is used, the composite can be dried or dried and calcined in between impregnations. The first component can be impregnated onto the carrier either prior to, simultaneously with, or after the platinum-group metal component, although not necessarily with equivalent results.

A second component, a platinum-group metal, is an essential ingredient of the catalyst. The second component comprises at least one of platinum, palladium, ruthenium, rhodium, iridium, or osmium; platinum is preferred, and it is especially preferred that the platinum-group metal consists essentially of platinum. The platinum-group metal component may exist within the final catalytic composite as a compound such as an oxide, sulfide, halide, oxyhalide, etc., in chemical combination with one or more of the other ingredients of the composite or as the metal. Amounts in the range of from about 0.01 to about 2-wt. % platinum-group metal component, on an elemental basis, are effective, and a range of from about 0.1 to about 1-wt. % platinum-group metal component, on an elemental basis is preferred. Best results are obtained when substantially all of the platinum-group metal is present in the elemental state.

The second component, a platinum-group metal component, is deposited on the composite using the same means as for the first component described above. Illustrative of the decomposable compounds of the platinum group metals are chloroplatinic acid, ammonium chloroplatinate, bromoplatinic acid, dinitrodiamino platinum, sodium tetranitroplatinate, rhodium trichloride, hexa-amminerhodium chloride, rhodium carbonylchloride, sodium hexanitrorhodate, chloropalladic acid, palladium chloride, palladium nitrate, diamminepalladium hydroxide, tetraamminepalladium chloride, hexachloroiridate (IV) acid, hexachloroiridate (III) acid, ammonium hexachloroiridate (III), ammonium aquo-hexachloroiridate (IV), ruthenium tetrachloride, hexachlororuthenate, hexa-ammineruthenium chloride, osmium trichloride and ammonium osmium chloride. The second component, a platinum-group component, is deposited on the support either before, after, or simultaneously with sulfate and/or the first component though not necessarily with equivalent results. It is preferred that the platinum-group component is deposited on the support either after or simultaneously with sulfate and/or the first component.

In addition to the first and second components above, the catalyst may optionally further include a third component of iron, cobalt, nickel, rhenium or mixtures thereof. Iron is preferred, and the iron may be present in amounts ranging from about 0.1 to about 5-wt. % on an elemental basis. The third component, such as iron, may function to lower the amount of the first component, such as gallium or indium, needed in the optimal formulation. The third component may be deposited on the composite using the same means as for the first and second components as described above. When the third component is iron, suitable compounds would include iron nitrate, iron halides, iron sulfate and any other soluble iron compound.

Additional optional third components include one or more of the following, a europium, terbium, holmium, erbium, thulium, ytterbium, or yttrium component, which may be present in amounts ranging from about 0.1 to about 5-wt. % on an elemental basis. Ytterbium is preferred. The additional component, such as ytterbium, may function to lower the amount of the first component, such as gallium or indium, needed in the optimal formulation. These additional component(s) may be deposited on the composite using the same means as for the first and second components as described above. When the additional component is ytterbium, suitable compounds would include a nitrate, halides, or sulfate of ytterbium and any other soluble ytterbium compound. Any one or combination of two or more of the third components described above, iron, cobalt, nickel, rhenium, europium, terbium, holmium, erbium, thulium, ytterbium, and yttrium, may be incorporated into the catalytic composite.

The catalytic composite described above can be used as a powder or can be formed into any desired shapes such as pills, cakes, extrudates, powders, granules, spheres, etc., and they may be utilized in any particular size. The composite is formed into the particular shape by means well known in the art. In making the various shapes, it may be desirable to mix the composite with a binder. However, it must be emphasized that the catalyst may be made and successfully used without a binder. The binder, when employed, usually comprises from about 0.1 to 50 mass-%, preferably from about 5 to 20 mass-%, of the finished catalyst. Refractory inorganic oxides are suitable binders. Examples of binders without limitation are silicas, alumina, silica-alumina, magnesia, zirconium, and mixtures thereof are suitable binder materials of the present invention. A preferred binder material is alumina, with eta- and/or especially gamma-alumina being favored. Usually the composite and optional binder are mixed along with a peptizing agent such as HCl, $HNO_3$, KOH, etc. to form a homogeneous mixture which is formed into a desired shape by forming means well known in the art. These forming means include extrusion, spray drying, oil dropping, marumarizing, conical screw mixing, etc. Extrusion means include screw extruders and extrusion presses. The forming means will determine how much water, if any, is added to the mixture. Thus, if extrusion is used, then the mixture should be in the form of a dough, whereas if spray drying or oil dropping is used, then enough water needs to be present in order to form a slurry. These particles are calcined at a temperature of about 260° C. to about 650° C. for a period of about 0.5 to about 2 hours.

The catalytic composites of the present invention either as synthesized or after calcination can be used as catalysts in hydrocarbon conversion processes. Calcination is required to form zirconium oxide from zirconium hydroxide. Hydrocarbon conversion processes are well known in the art and include cracking, hydrocracking, alkylation of both aromatics and isoparaffins, isomerization, polymerization, reforming, dewaxing, hydrogenation, dehydrogenation, transalkylation, dealkylation, hydration, dehydration, hydrotreating, hydrodenitrogenation, hydrodesulfurization, methanation, ring opening, and syngas shift processes. Specific reaction conditions and the types of feeds, which can be used in these processes, are set forth in U.S. Pat. Nos. 4,310,440 and 4,440,871 which are incorporated by reference. A preferred hydrocarbon conversion process is the isomerization of paraffins.

In a paraffin isomerization process, common naphtha feedstocks boiling within the gasoline range contain paraffins, naphthenes, and aromatics, and may comprise small amounts of olefins. Feedstocks which may be utilized include straight-run naphthas, natural gasoline, synthetic naphthas, thermal gasoline, catalytically cracked gasoline, partially reformed naphthas or raffinates from extraction of aromatics. The feedstock essentially is encompassed by the range of a full-range naphtha, or within the boiling point range of 0° to 230° C. Usually the feedstock is light naphtha having an initial boiling point of about 10° to 65° C. and a final boiling point from about 75° to 110° C.; preferably, the final boiling point is less than about 95° C.

The principal components of the preferred feedstock are alkanes and cycloalkanes having from 4 to 7 carbon atoms per molecule ($C_4$ to $C_7$), especially $C_5$ to $C_6$, and smaller amounts of aromatic and olefinic hydrocarbons also may be present. Usually, the concentration of $C_7$ and heavier components is less than about 20 mass-% of the feedstock. Although there are no specific limits to the total content in the feedstock of cyclic hydrocarbons, the feedstock generally contains between about 2 and 40 mass-% of cyclics comprising naphthenes and aromatics. The aromatics contained in the naphtha feedstock, although generally amounting to less than the alkanes and cycloalkanes, may comprise from 2 to 20 mass-% and more usually from 5 to 10 mass-% of the total. Benzene usually comprises the principal aromatics constituent of the preferred feedstock, optionally along with smaller amounts of toluene and higher-boiling aromatics within the boiling ranges described above.

Contacting within the isomerization zones may be effected using the catalyst in a fixed-bed system, a moving-bed system, a fluidized-bed system, or in a batch-type operation. A fixed-bed system is preferred. The reactants may be contacted with the bed of catalyst particles in either upward, downward, or radial-flow fashion. The reactants may be in the liquid phase, a mixed liquid-vapor phase, or a vapor phase when contacted with the catalyst particles, with excellent results being obtained by application of the present invention to a primarily liquid-phase operation. The isomerization zone may be in a single reactor or in two or more separate reactors with suitable means therebetween to ensure that the desired isomerization temperature is maintained at the entrance to each zone. Two or more reactors in sequence are preferred to enable improved isomerization through control of individual reactor temperatures and for partial catalyst replacement without a process shutdown.

Isomerization conditions in the isomerization zone include reactor temperatures usually ranging from about 40° to 250° C. Lower reaction temperatures are generally preferred in order to favor equilibrium mixtures having the highest concentration of high-octane highly branched isoalkanes and to minimize cracking of the feed to lighter hydrocarbons. Temperatures in the range of about 100° to about 200° C. are preferred in the process of the present invention. Reactor operating pressures generally range from about 100 kPa to 10 MPa absolute, preferably between about 0.3 and 4 MPa. Liquid hourly space velocities range from about 0.2 to about 25 $hr^{-1}$, with a range of about 0.5 to 15 $hr^{-1}$ being preferred.

Hydrogen is admixed with or remains with the paraffinic feedstock to the isomerization zone to provide a mole ratio of hydrogen to hydrocarbon feed of from about 0.01 to 20, preferably from about 0.05 to 5. The hydrogen may be supplied totally from outside the process or supplemented by hydrogen recycled to the feed after separation from the reactor effluent. Light hydrocarbons and small amounts of inerts such as nitrogen and argon may be present in the hydrogen. Water should be removed from hydrogen supplied from outside the process, preferably by an adsorption system as is known in the art. In a preferred embodiment, the hydrogen to hydrocarbon mol ratio in the reactor effluent is equal to or less than 0.05, generally obviating the need to recycle hydrogen from the reactor effluent to the feed.

Upon contact with the catalyst, at least a portion of the paraffinic feedstock is converted to desired, higher octane, isoparaffin products. The catalyst of the present invention provides the advantages of high activity and improved stability. When the first component is selected to be ytterbium, the catalyst of the present invention has the additional advantage of increased ring opening activity.

The isomerization zone generally also contains a separation section, optimally comprising one or more fractional distillation columns having associated appurtenances and separating lighter components from an isoparaffin-rich product. Optionally, a fractionator may separate an isoparaffin concentrate from a cyclics concentrate with the latter being recycled to a ring-cleavage zone.

Preferably part or all of the isoparaffin-rich product and/or the isoparaffin concentrate are blended into finished gasoline along with other gasoline components from refinery processing including, but not limited to, one or more of butanes, butenes, pentanes, naphtha, catalytic reformate, isomerate, alkylate, polymer, aromatic extract, heavy aromatics, gasoline from catalytic cracking, hydrocracking, thermal cracking, thermal reforming, steam pyrolysis and coking, oxygenates such as methanol, ethanol, propanol, isopropanol, tert-butyl alcohol, sec-butyl alcohol, methyl tertiary butyl ether, ethyl tertiary butyl ether, methyl tertiary amyl ether and higher alcohols and ethers, and small amounts of additives to promote gasoline stability and uniformity, avoid corrosion and weather problems, maintain a clean engine and improve driveability.

The following examples serve to illustrate certain specific embodiments of the present invention. These examples should not, however, be construed as limiting the scope of the invention as set forth in the claims. There are many possible other variations, as those of ordinary skill in the art will recognize, which are within the scope of the invention.

EXAMPLE 1

Catalyst samples of Table 1 were prepared starting with zirconium hydroxide that had been prepared by precipitating zirconyl nitrate with ammonium hydroxide at 65° C. The zirconium hydroxide was dried at 120° C., ground to 40–60 mesh. Multiple discrete portions of the zirconium hydroxide were prepared. Solutions of either ammonium sulfate or a metal salt (component 1) were prepared and added to the portions of zirconium hydroxide. The materials were agitated briefly and then dried with 80–100° C. air while rotating. The impregnated samples were then dried in a muffle oven at 150° C. for two hours under air. Optionally, solutions of either ammonium sulfate or a metal salt (component 2, where component 2 is not the same as component 1) were prepared and added to the dried materials. The samples were briefly agitated and dried while rotating. The samples were then calcined at 600–700° C. for 5 hours. The final impregnation solutions of chloroplatinic acid were prepared and added to the solids. The samples were agitated and dried while rotating as before. The samples were finally calcined at 525° C. in air for 2 hours. Table 1 shows the resulting catalysts.

TABLE 1

| Modifier | Modifier Level, mass % | Fe mass % | Yb mass % | Pt mass % | SO$_4$ mass % |
|---|---|---|---|---|---|
| Ga | 0.5 | 0 | 0 | 0.25 | 7 |
| Ga | 0.5 | 0 | 0 | 0.75 | 7 |
| Ga | 1.5 | 0 | 0 | 0.25 | 7 |
| Ga | 1.5 | 0 | 0 | 0.75 | 7 |
| Ga | 0.5 | 1.5 | 0 | 0.25 | 7 |
| Ga | 0.5 | 1.5 | 0 | 0.75 | 7 |
| Ga | 1.5 | 1.5 | 0 | 0.25 | 7 |
| Ga | 1.5 | 1.5 | 0 | 0.75 | 7 |
| Ga | 0.5 | 0 | 1.5 | 0.25 | 7 |
| Ga | 0.5 | 0 | 1.5 | 0.75 | 7 |
| Ga | 1.5 | 0 | 1.5 | 0.25 | 7 |
| Ga | 1.5 | 0 | 1.5 | 0.75 | 7 |
| In | 0.5 | 0 | 0 | 0.25 | 7 |
| In | 0.5 | 0 | 0 | 0.75 | 7 |
| In | 1.5 | 0 | 0 | 0.25 | 7 |
| In | 1.5 | 0 | 0 | 0.75 | 7 |
| In | 0.5 | 1.5 | 0 | 0.25 | 7 |
| In | 0.5 | 1.5 | 0 | 0.75 | 7 |
| In | 1.5 | 1.5 | 0 | 0.25 | 7 |
| In | 1.5 | 1.5 | 0 | 0.75 | 7 |
| In | 0.5 | 0 | 1.5 | 0.25 | 7 |
| In | 0.5 | 0 | 1.5 | 0.75 | 7 |
| In | 1.5 | 0 | 1.5 | 0.25 | 7 |
| In | 1.5 | 0 | 1.5 | 0.75 | 7 |

EXAMPLE 2

Figure 2:
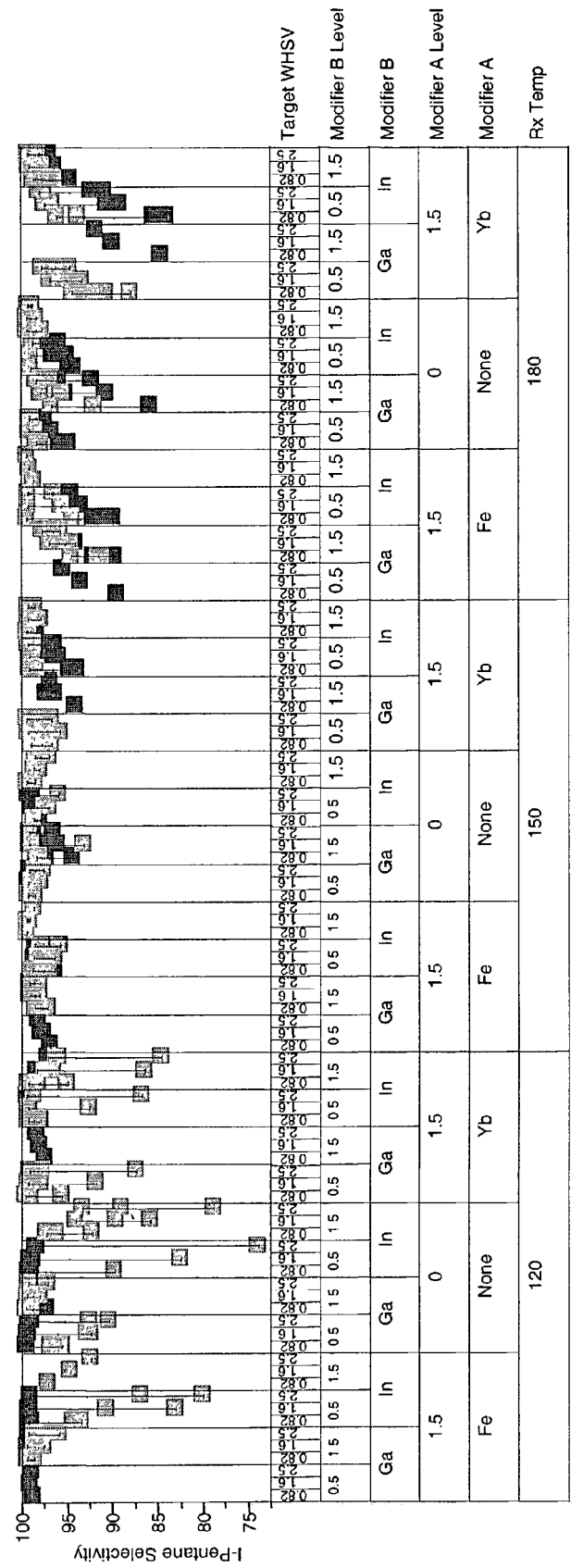
FIG. 2 is a plot of the isopentane selectivity observed at different reaction temperatures and weight hourly space velocities for each of the catalysts of Example 2 having 0.25 wt-% platinum.
Figure 3:
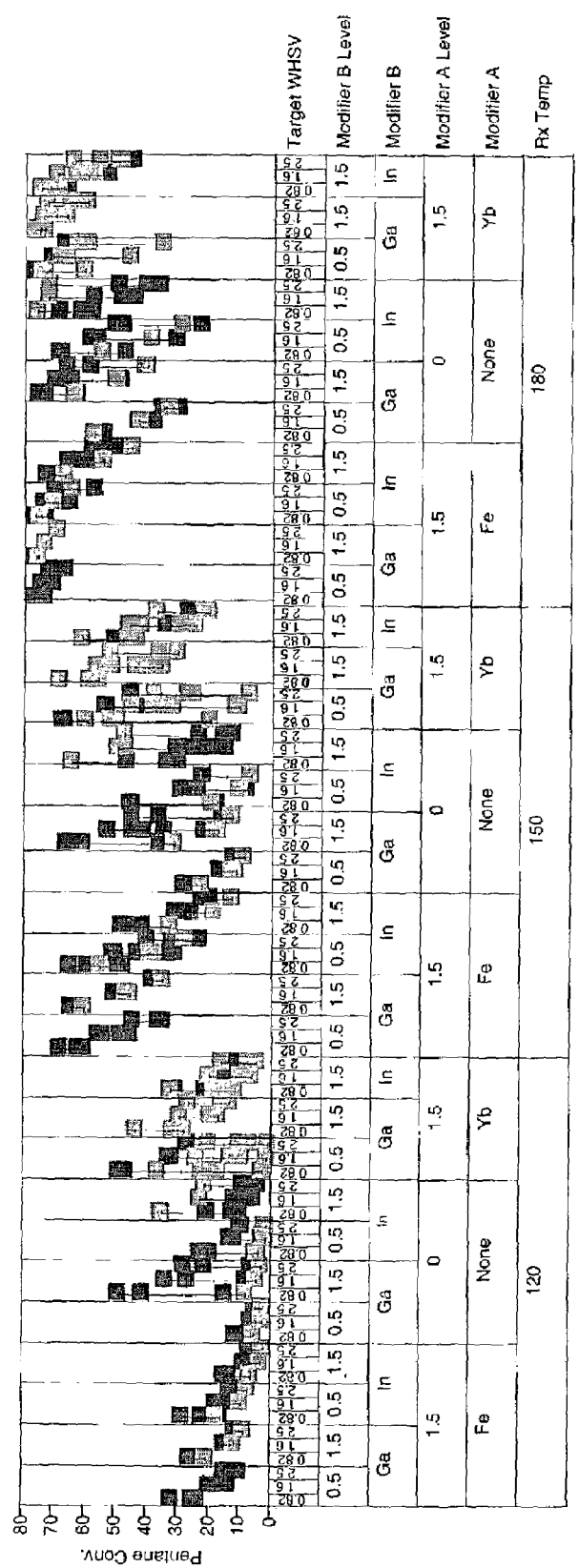
FIG. 3 is a plot of percent pentane conversion observed at different reaction temperatures and weight hourly space velocities for each of the catalysts of Example 2 having 0.75 wt-% platinum.
Figure 4:
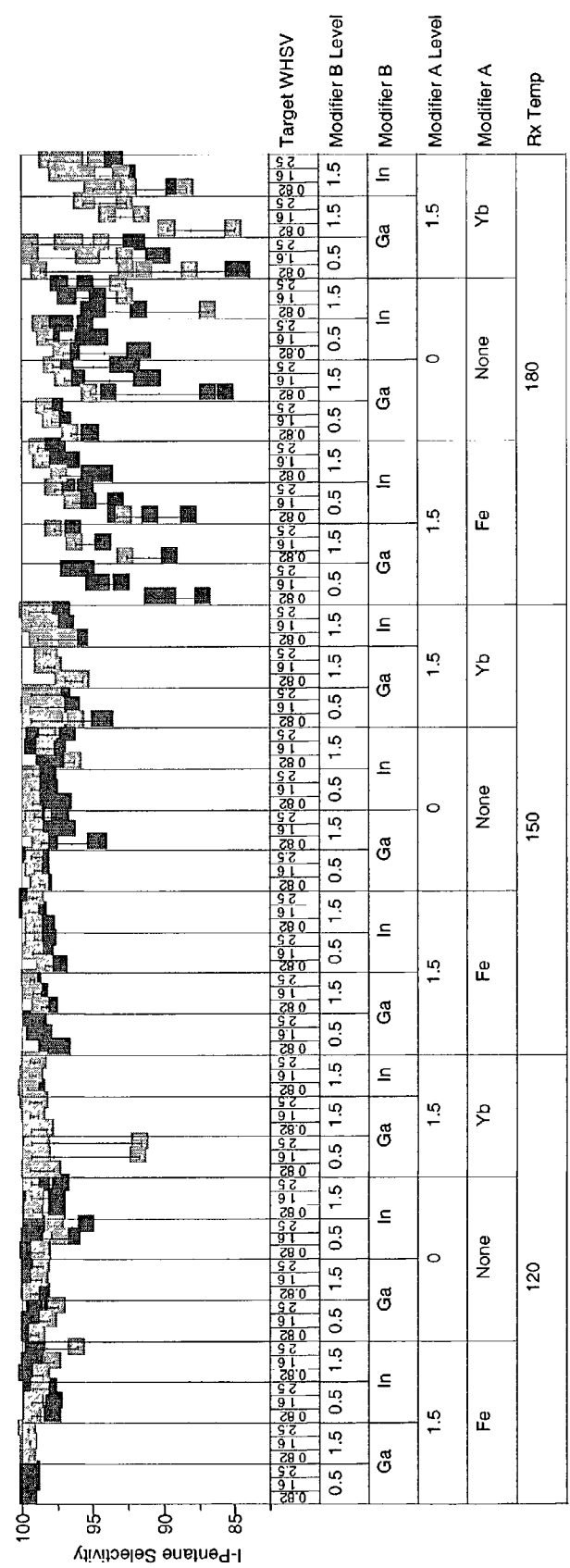
FIG. 4 is a plot of the isopentane selectivity observed at different reaction temperatures and weight hourly space velocities for each of the catalysts of Example 2 having 0.75 wt-% platinum.

Catalysts were prepared as described in Example 1 containing 0.5 and 1.5 wt. % modifier, 0.25 wt. % and 0.75 wt % platinum, and 7 wt. % sulfate. More catalysts were prepared as above, but additionally comprising 1.5 wt. % iron or ytterbium. Approximately 95 mg of each sample was loaded into a multi-unit reactor assay. The catalysts were pretreated in air at 450° C. for 2–6 hours and reduced at 200° C. in H$_2$ for 0.5–2 hours. 8 wt. % pentane in hydrogen was then passed over the samples at 120° C., 150° C., and 180° C. approximately 1 atm, and 0.82, 1.6, and 2.5 hr$^{-1}$ WHSV (based on pentane only). The products were analyzed using online gas chromatographs and the results are shown in FIGS. 1–4. FIG. 1 is a plot of percent pentane conversion observed for each of the catalysts having 0.25 wt-% platinum at the different reaction temperatures and weight hourly space velocities. FIG. 2 is a plot of the isopentane selectivity observed for each of the catalysts having 0.25 wt.-% platinum at the different reaction temperatures and weight hourly space velocities. FIG. 3 is a plot of percent pentane conversion observed for each of the catalysts having 0.75 wt-% platinum at the different reaction temperatures and weight hourly space velocities. FIG. 4 is a plot of the isopentane selectivity observed for each of the catalysts having 0.75 wt.-% platinum at the different reaction temperatures and weight hourly space velocities.

In general, FIGS. 1–4 show that the activity of the catalysts can be controlled through controlling the identity and concentration of the specified components. For example, the data shows that catalysts having both gallium and ytterbium are the most active. Those catalysts having gallium are more active with increasing amounts of gallium. On the other hand, indium attenuates the catalysts; increasing the amount of indium decreases the activity of the catalyst.

The invention claimed is:

1. A catalyst consisting essentially of a support comprising a sulfated oxide or hydroxide of at least one of the elements of Group IVB (IUPAC 4), the support having deposited thereon; a first component comprising at least one Group III A (IUPAC 13) component; a second component comprising at least one platinum-group metal component; and optionally a third component selected from the group consisting of iron, cobalt, nickel, rhenium, europium, terbium, holmium, erbium, thulium, ytterbium, yttrium, and combinations thereof.

2. The catalyst of claim 1 wherein the first component comprises from about 0.01 to about 10 mass-%, on an elemental basis, of the catalyst.

3. The catalyst of claim 1 wherein the second component comprises from about 0.01 to about 2 mass-%, on an elemental basis, of the catalyst.

4. The catalyst of claim 1 wherein the element of Group IVB (IUPAC 4) comprises zirconium.

5. The catalyst of claim 1 wherein the catalyst comprises from about 0.5 to about 5 mass-% sulfur on an elemental basis.

6. The catalyst of claim 1 wherein the atomic ratio of the first component to the second component is at least about 2.

7. The catalyst of claim 1 further comprising from about 2 to about 25 mass-% of a refractory inorganic-oxide binder.

8. The catalyst of claim 7 wherein the refractory inorganic-oxide binder comprises alumina.

9. The catalyst of claim 1 wherein the first component consists essentially of one single Group III A (IUPAC 13) component and the second component consists essentially of one single metal selected from the platinum-group metals.

10. The catalyst of claim 1 wherein the first component is selected from the group consisting of gallium, indium, and the combination thereof.

11. The catalyst of claim 1 wherein the second component is platinum.

12. The catalyst of claim 1 wherein the third component comprises from about 0.1 to about 5 wt-%, on an elemental basis, of the catalyst.

13. A hydrocarbon conversion catalyst consisting essentially of a support comprising a sulfated oxide or hydroxide of zirconium having deposited thereon; from about 0.01 to about 10 mass-%, on an elemental basis, of a Group III A (IUPAC 13) component selected from the group consisting of gallium, indium, and mixtures thereof; from about 0.01 to about 2 mass-%, on an elemental basis, of a platinum component; and optionally, from about 0.1 to about 5 mass-% of a third component selected from the group consisting of iron, cobalt, nickel, rhenium, europium, terbium, holmium, erbium, thulium, ytterbium, yttrium, and combinations thereof.

14. A process for the preparation of a catalyst suitable for hydrocarbon conversion consisting essentially of a sulfated support comprising at least one of the oxides and hydroxides of the elements of Group IVB (IUPAC 4), a first component comprising at least one Group III A (IUPAC 13) components, a second component comprising at least one platinum-group metal, and optionally a third component selected from the group consisting of iron, cobalt, nickel, rhenium, europium, terbium, holmium, erbium, thulium, ytterbium, yttrium, and combinations thereof, the process comprising sulfating an oxide or hydroxide of at least one element of Group IVB (IUPAC 4) to form a sulfated support; depositing on the sulfated support, the first component; depositing on the sulfated support, the second component; and optionally depositing on the sulfated support, the third component to form said catalyst.

15. A process for converting hydrocarbons by contacting a feed with a solid acid catalyst to give a converted product, the catalyst consisting essentially of a support comprising a sulfated oxide or hydroxide of at least an element of Group IVB (IUPAC 4), a first component comprising at least one Group III A (IUPAC 13) component, a second component comprising at least one platinum-group metal, and optionally a third component selected from the group consisting of iron, cobalt, nickel, rhenium, europium, terbium, holmium, erbium, thulium, ytterbium, yttrium, and combinations thereof.

16. The process of claim 15 wherein the hydrocarbon conversion process is selected from the group consisting of cracking, hydrocracking, aromatic alkylation, isoparaffin alkylation, isomerization, polymerization, reforming, dewaxing, hydrogenation, dehydrogenation, transalkylation, dealkylation, hydration, dehydration, hydrotreating, hydrodenitrogenation, hydrodesulfurization, methanation, ring opening, and syngas shift.

17. A process for the isomerization of a paraffinic feedstock to obtain a product having an increased isoparaffin content comprising contacting the paraffinic feedstock in an isomerization zone maintained at isomerization conditions comprising a temperature from about 40 to about 250° C., a pressure from about 100 kPa to about 10 MPa and a liquid hourly space velocity from about 0.2 to about 25 hr$^{-1}$ with a solid acid isomerization catalyst consisting essentially of a sulfated support comprising an oxide or hydroxide of elements of Group IVB (IUPAC 4), a first component comprising at least one Group III A (IUPAC 13) component, a second component comprising at least one platinum-group metal, and optionally a third component selected from the group consisting of iron, cobalt, nickel, rhenium, europium, terbium, holmium, erbium, thulium, ytterbium, yttrium, and combinations thereof, and recovering an isoparaffin-rich product.

18. The process of claim 17 wherein free hydrogen is present in the isomerization zone in an amount from about 0.01 to about 20 moles per mole of $C_5+$ hydrocarbons present in the zone.

19. The process of claim 17 wherein the isomerization conditions comprise a temperature from about 100 to about 200° C., a pressure from about 300 kPa to about 4 MPa, and a liquid hourly space velocity from about 0.5 to about 15 hr$^{-1}$, and wherein free hydrogen is present in the isomerization zone in an amount from about 0.05 to about 5 moles per mole of $C_5+$ hydrocarbons present in the zone.

20. The process of claim 17 wherein the isomerization catalyst further comprises a refractory inorganic-oxide binder.

21. The process of claim 20 wherein the refractory inorganic-oxide binder comprises alumina.

22. The process of claim 17 wherein the atomic ratio of the first component to the second component is at least about 2.

23. The process of claim 17 wherein the first component is selected from the group consisting of gallium, indium, or mixtures thereof and the second component is platinum.

24. The process of claim 17 wherein the third component comprises from about 1 to about 5 wt. % on an elemental basis, of the catalyst.

25. The process of claim 17 further comprising using at least a portion of the isoparaffin-rich product to blend a gasoline product.

* * * * *